United States Patent
Krupica et al.

(10) Patent No.: US 9,138,195 B2
(45) Date of Patent: Sep. 22, 2015

(54) CONTACTLESS COMMUNICATION SIGNAL TRANSFER

(75) Inventors: Libor Krupica, Nashua, NH (US); Wei Ye, Westford, MA (US)

(73) Assignee: Analogic Corporation, Peabody, MA (US)

( * ) Notice: Subject to any disclaimer, the term of this patent is extended or adjusted under 35 U.S.C. 154(b) by 584 days.

(21) Appl. No.: 13/453,203

(22) Filed: Apr. 23, 2012

(65) Prior Publication Data

US 2013/0279647 A1  Oct. 24, 2013

(51) Int. Cl.
| | |
|---|---|
| A61B 6/03 | (2006.01) |
| H01Q 1/36 | (2006.01) |
| H01Q 1/38 | (2006.01) |
| A61B 6/00 | (2006.01) |
| G01N 23/04 | (2006.01) |
| H01Q 3/00 | (2006.01) |
| H01Q 3/04 | (2006.01) |
| H01Q 5/25 | (2015.01) |

(52) U.S. Cl.
CPC . *A61B 6/032* (2013.01); *A61B 6/56* (2013.01); *A61B 6/563* (2013.01); *G01N 23/046* (2013.01); *H01Q 1/36* (2013.01); *H01Q 1/38* (2013.01); *H01Q 3/005* (2013.01); *H01Q 3/04* (2013.01); *H01Q 5/25* (2015.01); *G01N 2223/419* (2013.01)

(58) Field of Classification Search
CPC .......... A61B 6/032; A61B 6/56; A61B 6/563; G01N 23/046; H01Q 1/38; H01Q 5/0003; H01Q 9/0407; H01Q 1/243; H01Q 7/00; H01Q 9/285; H01A 1/36
USPC ................................ 378/15, 91; 343/700 MS
See application file for complete search history.

(56) References Cited

U.S. PATENT DOCUMENTS

| | | | | |
|---|---|---|---|---|
| 4,646,086 | A * | 2/1987 | Helzel | 340/870.29 |
| 5,530,422 | A * | 6/1996 | Harrison | 340/500 |
| 5,530,423 | A * | 6/1996 | Harrison | 340/500 |
| 5,530,424 | A * | 6/1996 | Harrison et al. | 340/500 |
| 5,530,425 | A * | 6/1996 | Harrison | 340/500 |
| 5,577,026 | A | 11/1996 | Gordon et al. | |
| 5,579,357 | A * | 11/1996 | Harrison | 378/4 |
| 5,600,697 | A * | 2/1997 | Harrison | 378/15 |
| 5,646,962 | A * | 7/1997 | Harrison | 375/308 |
| 6,104,349 | A * | 8/2000 | Cohen | 343/702 |
| 6,111,545 | A * | 8/2000 | Saari | 343/702 |
| 6,130,651 | A * | 10/2000 | Yanagisawa et al. | 343/895 |
| 6,140,975 | A * | 10/2000 | Cohen | 343/846 |
| 6,181,766 | B1 * | 1/2001 | Pearson et al. | 378/15 |
| 6,292,919 | B1 * | 9/2001 | Fries et al. | 714/758 |

(Continued)

*Primary Examiner* — Allen C. Ho
(74) *Attorney, Agent, or Firm* — Cooper Legal Group LLC (57) ABSTRACT

Among other things, one or more data-links for transferring information between a stationary unit and a movable (e.g., rotating) unit, or between two movable units without contact between the units is provided. A transmitting antenna of a data-link comprises at least two capacitive conducting portions, a first portion configured to conduct signals having a first frequency range (e.g., a higher frequency range) and a second portion configured to conduct signals having a second frequency range (e.g., a lower frequency range). The second portion is comprised of a plurality of members (e.g., conductive plates) arranged to create a substantially continuous electrically conductive structure (e.g., although respective members may not be in physical contact with adjacent members). In this way, a loss of capacitance in a transition between two adjacent members is reduced to provide for transferring information at lower frequencies where a higher capacitance is desirable, for example.

20 Claims, 6 Drawing Sheets

(56) References Cited

U.S. PATENT DOCUMENTS

| | | | |
|---|---|---|---|
| 6,337,663 B1* | 1/2002 | Chi-Ming | 343/702 |
| 6,337,667 B1* | 1/2002 | Ayala et al. | 343/795 |
| 6,459,413 B1* | 10/2002 | Tseng et al. | 343/702 |
| 6,862,299 B2* | 3/2005 | Popescu | 370/516 |
| 6,995,717 B2* | 2/2006 | Ryu | 343/702 |
| 7,050,616 B2* | 5/2006 | Hsieh et al. | 382/131 |
| 7,079,619 B2* | 7/2006 | Katcha et al. | 378/15 |
| 7,148,846 B2* | 12/2006 | Qi et al. | 343/700 MS |
| 7,240,251 B2* | 7/2007 | Popescu | 714/704 |
| 7,274,765 B2* | 9/2007 | Krumme et al. | 378/15 |
| 7,411,556 B2* | 8/2008 | Sanz et al. | 343/702 |
| 7,421,058 B2* | 9/2008 | Popescu et al. | 378/20 |
| 7,423,257 B2* | 9/2008 | Popescu | 250/231.14 |
| 7,466,791 B2* | 12/2008 | Krumme | 378/15 |
| 7,599,467 B2* | 10/2009 | Popescu | 378/21 |
| 7,755,055 B2* | 7/2010 | Schilling | 250/370.09 |
| 7,760,851 B2* | 7/2010 | Festag et al. | 378/15 |
| 7,761,115 B2* | 7/2010 | Castaneda et al. | 455/562.1 |
| 7,807,981 B2* | 10/2010 | Frach et al. | 250/492.1 |
| 7,880,569 B2 | 2/2011 | Krumme et al. | |
| 7,889,836 B2* | 2/2011 | Popescu | 378/15 |
| 7,899,150 B2* | 3/2011 | Beyerlein et al. | 378/15 |
| 7,957,786 B2* | 6/2011 | Katcha et al. | 600/407 |
| 8,072,335 B2* | 12/2011 | Duzdar et al. | 340/572.7 |
| 8,248,312 B2* | 8/2012 | Guan et al. | 343/702 |
| 8,248,313 B2* | 8/2012 | Marcher et al. | 343/702 |
| 8,260,019 B2* | 9/2012 | Chandra | 382/131 |
| 8,310,398 B2* | 11/2012 | Deng et al. | 343/700 MS |
| 8,368,599 B2* | 2/2013 | Lim et al. | 343/700 MS |
| 8,508,414 B2* | 8/2013 | Cho | 343/702 |
| 8,525,747 B2* | 9/2013 | Focke et al. | 343/770 |
| 8,552,918 B2* | 10/2013 | Lee et al. | 343/826 |
| 8,570,223 B2* | 10/2013 | Arslan et al. | 343/700 MS |
| 8,594,480 B2* | 11/2013 | Krumme et al. | 385/147 |
| 8,648,754 B2* | 2/2014 | Kim et al. | 343/729 |
| 8,786,497 B2* | 7/2014 | Sharawi | 343/700 MS |
| 8,890,750 B2* | 11/2014 | Mak et al. | 343/700 MS |

* cited by examiner

CONTACTLESS COMMUNICATION SIGNAL TRANSFER

BACKGROUND

The present application relates to the transference of information over an airgap separating a receiver from a transmitter. It finds particular application in the context of computed tomography (CT) imaging modalities, which may be utilized in medical, security, and/or industrial applications, for example, where at least one of the transmitter and the receiver is located on a rotating gantry and an airgap separating a transmitting antenna from a receiving antenna is small (e.g., 20 mm or less). However, it may also apply to other applications, such as explosive detection machines, radar antennas, etc. where communication signals are wirelessly transferred between a transmitter and a receiver.

Today, CT and other radiation imaging modalities (e.g., single-photon emission computed tomography (SPECT), mammography, projection radiography, etc.) are useful to provide information, or images, of interior aspects of an object under examination. Generally, the object is exposed to radiation comprising photons (e.g., such as x-rays, gamma rays, etc.), and an image(s) is formed based upon the radiation absorbed and/or attenuated by the interior aspects of the object, or rather an amount of photons that is able to pass through the object. Generally, highly dense aspects of the object absorb and/or attenuate more radiation than less dense aspects, and thus an aspect having a higher density, such as a bone or metal, for example, will be apparent when surrounded by less dense aspects, such as muscle or clothing.

Some radiation imaging modalities, such as CT, are configured to generate volumetric data corresponding to an object under examination. To generate this volumetric data, the CT imaging modality is typically configured to rotate a radiation source and detector array about the object under examination (e.g., causing the object to be viewed from a plurality of angles). For example, the radiation source and/or detector array may be mounted to a rotating gantry (at times referred to as a rotor) configured for rotation relative to a stationary unit (at times referred to as a stator) configured to support the rotating gantry.

Given that the radiation source and detector array are mounted on the rotating gantry, power and control information (e.g., instructing the radiation source and/or other electronic components how to operate) are typically supplied to the rotating gantry from the stationary unit. Moreover, imaging data (e.g., data generated in response to the detection of radiation by the detector array) is typically transferred from the rotating gantry to the stationary unit (e.g., for further processing and/or to be displayed to security/medical personnel). It may be appreciated that the volume of data transferred, particularly with respect imaging data, may be quite large. For example, some imaging modalities may require transfer speeds of up to 5 gigabits per second (e.g., particularly if the rotating gantry does not comprise a storage medium to temporarily store data until it can be transferred).

Conventionally, slip-ring assemblies have been used to transfer power and/or information (e.g., control information and/or imaging data) between the stationary unit and the rotating gantry or more generally between a movable unit and a stationary unit (or between two movable units) through the physical contact of two materials (e.g., via a sliding contact). For example, a slip-ring attached to the stationary member may comprise metal brushes that are configured to physically contact electrically conductive surfaces (e.g., metal brushes) comprised on a slip-ring attached to the movable unit, allowing power and/or information to be transferred between the stationary unit and the movable unit.

While the use of slip-ring assemblies has proven effective for transferring power and/or information between a stationary unit and a movable unit (e.g., such as a rotating gantry) and/or between two movable units, conventional slip-ring assemblies may generate dust or particles (e.g., as metal brushes wear), may be unreliable (e.g., again as contact surfaces, such as metal brushes, wear), and/or may be noisy (e.g., as surfaces rub against one another), which may cause interference with some procedures (e.g., CT imaging). Other drawbacks of slip-ring assemblies may include cost and complexity of manufacture due to special materials and/or mechanical precision that may be required.

More recently, contactless assemblies have been devised to transfer the data (e.g., or electrical signals derived from the data) between the rotating gantry and the stationary unit. For example, U.S. Pat. No. 5,577,026 (assigned to Analogic Corporation) and U.S. Pat. No. 7,760,851 (assigned to Siemens Aktiengesellschaft and Schleifring and Apparatebau GmbH), at least some of which are respectively incorporated herein by reference, describe two different approaches to contactless assemblies for transferring data. While such assemblies overcome many of the aforementioned drawbacks to a slip-ring assembly, the amount of data capable of being transferred via the foregoing contactless assemblies is limited. For example, U.S. Pat. No. 7,760,851 appears to describe transferring data at a transfer speed of, at most, 1.5 Gbps. As radiation imaging modalities continue to develop (e.g., and transition to photon counting imaging modalities), data may be required to be transferred at much faster speeds. Further, data may be required to be transferred at a wider range of frequencies than either of the aforementioned contactless assemblies is configured to handle.

SUMMARY

Aspects of the present application address the above matters, and others. According to one aspect, a wide frequency bandwidth transmitting element for a radiation imaging modality is provided. The transmitting element comprises at least first and second conducting portions. The first conducting portion is configured to conduct signals having a first frequency range and the second conducting portion is configured to conduct signals having a second frequency range, the second frequency range comprising at least some frequencies that are less than at least some frequencies comprised in the first frequency range. The first conducting portion is operably coupled to the second conducting portion. The second conducting portion comprises a plurality of members, the members arranged such that at least some of a first member overlaps at least some of a second member.

According to another aspect, a data-link for a CT imaging modality is provided. The data-link comprises a transmitter, comprising a transceiver component configured to convert an optical signal indicative of an examination of an object by the CT imaging modality into an electrical signal, a clock and data recovery component configured to recover a clock from the electrical signal and to generate an electrical signal with the recovered clock, and a power divider component configured to divide the electrical signal with the recovered clock into two signals. The data-link also comprises a transmitting antenna comprising at least two transmitting elements, a first transmitting element configured to radiate first radio waves in response to a first of the two signals and a second transmitting element configured to radiate second radio waves in response to a second of the two signals. The data-link further comprises a receiving antenna configured to receive the first and second radio waves, a first radio frequency signal being generated from the first radio waves and a second radio frequency signal being generated from the second radio waves. The data-link also comprises a receiver, comprising a radio frequency combining component configured to combine the first and second radio frequency signals and generate a combined radio frequency signal, a clock and data recovery component configured to recover a clock from the combined radio frequency signal and generate a combined radio frequency signal with the recovered clock, and a transceiver component configured to convert the combined radio frequency signal with the recovered clock to an optical signal.

According to another embodiment, a CT imaging modality is provided. The CT imaging modality comprises a rotating gantry configured to rotate about an object under examination. The rotating gantry comprises a radiation source configured to emit radiation towards the object under examination, a detector array configured to detect at least a portion of the emitted radiation and to generate analog signals indicative of the detected radiation, a data acquisition system configured to convert the analog signals into data, and a transmitting element configured to radiate radio waves in response to electrical signals, corresponding to at least some of the data, applied to the transmitting element. The transmitting element comprises at least first and second conducting portions. The first conducting portion is configured to conduct radio frequency signals having a first frequency range and the second conducting portion is configured to conduct radio frequency signals having a second frequency range, the second frequency range comprising at least some frequencies that are less than at least some frequencies comprised in the first frequency range. The first conducting portion is operably coupled to the second conducting portion. The second conducting portion is comprised of a plurality of members, the members arranged such that at least some of a first member overlaps at least some of a second member.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a communication system (at times referred to as a data-link) for transferring information between two (or more) units. Typically, at least one of the units is movable (e.g., rotating) relative to the other unit, and the two units are separated by an airgap (or gap of some other medium, material, etc.). The transmitting antenna of the data-link comprises at least two conducting portions. A first of the two conducting portions may perform as a first capacitive coupling and may be configured to conduct signals having a first frequency range (e.g., a high frequency range). A second of the two conducting portions may perform as a second capacitive coupling and may be configured to conduct signals having a second frequency range (e.g., a lower frequency range). Moreover, the second of the two conducting portions may be comprised of a plurality of members (e.g., plates) configured to at least partially overlap one another. By at least partially overlapping one another, a substantially electrically continuous structure may be formed to reduce the amount of capacitance lost in a transition of a signal from a first member of the second conducting portion to second member of the second conducting portion, for example. Moreover, it may be appreciated that the combination of the two conducting portions may create a wide frequency bandwidth antenna (e.g., to reduce attenuation at lower frequencies). The at least two conducting portions are, in one example, configured to achieve a data transfer rate of at least 1.5 Gbps (although slower and/or faster transfer speeds are also contemplated) and multiple antennas may be utilized to achieve even fast (or slower) transfer rates.

It may be appreciated that "noncontact," "contactless," and/or the like is used herein to refer to the ability to transfer information between or among bodies configured for relative movement, and should not be understood to necessarily preclude possible contact between or among such bodies for other purposes, including, for example, electrostatic discharge, exchange or transmission of data, mechanical drive or support, braking and safety mechanisms, low-voltage power transfer, and/or high-voltage power transfer, etc.

It may also be appreciated that in the present disclosure, except where otherwise clear from context, "gap" and "airgap" are used more or less interchangeably; although "airgap" may be used herein, as this should be understood to be mere deference to convention, it should be understood that such gaps are not limited to air, it being possible for vacuum, oil, and/or other fluid and/or gas, and/or sliding and/or roller bearings or other such contrivances permitting relative movement to completely or partially fill such spaces. Further, "radiation imaging modality" and/or the like is intended to describe how the imaging modality utilizes radiation to perform an examination.

Figure 1:
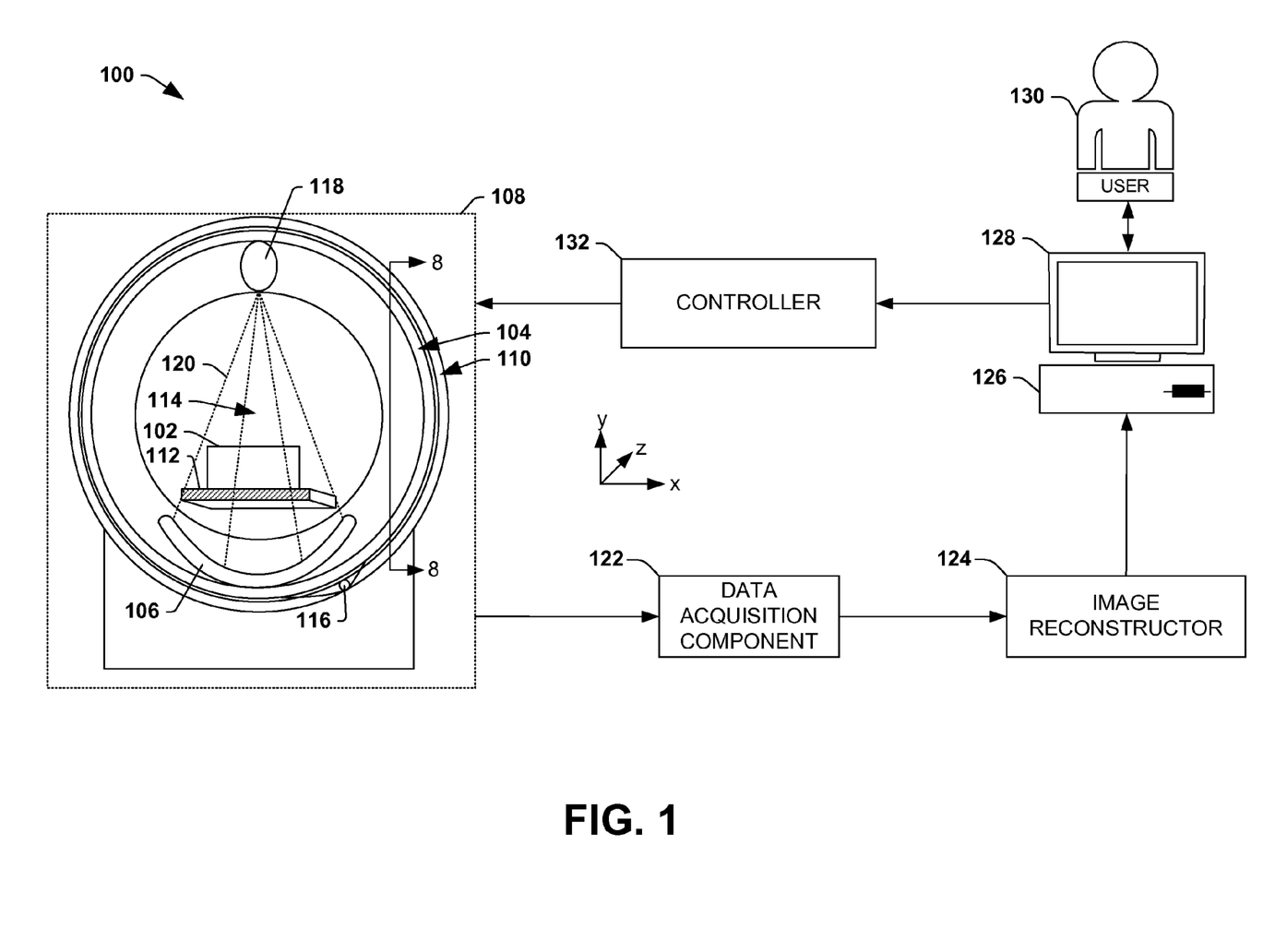
FIG. 1 is a schematic block diagram illustrating an example environment where a data-link such as described herein may be implemented.

FIG. 1 is an illustration of an example environment 100 where a wide frequency bandwidth antenna and/or data-link as provided for herein may be useful. More particularly, FIG. 1 illustrates an example computed tomography (CT) imaging modality that can be configured to acquire volumetric information regarding an object 102 under examination and generate two-dimensional, three-dimensional, and/or four-dimensional (e.g., temporal) images therefrom.

It may be appreciated that while a CT imaging modality is described herein, the instant application is not intended to be so limited. That is, to the extent practical, the instant application, including the scope of the claimed subject matter, is intended to be applicable to other apparatuses where a wide frequency bandwidth antenna and/or a data-link comprising such an antenna may be useful. More particularly, the instant application is applicable to other apparatuses where supplying communication information (e.g., control information, imaging information, etc.) to and/or from a movable unit of an apparatus would be useful. Moreover, the example environment 100 merely illustrates an example diagram and is not intended to be interpreted in a limiting manner, such as necessarily specifying the location, inclusion, and/or relative arrangement of the components described herein. For example, a data acquisition component 122 as illustrated in FIG. 1 may be part of a rotor 104 portion of an object examination apparatus 108, or more particularly may be part of a detector array 106, for example.

In the example environment 100, the object examination apparatus 108 is configured to examine one or more objects 102 (e.g., a series of suitcases at an airport, a human patient, etc.). The object examination apparatus 108 can comprise a rotor 104 (at times referred to as a rotating gantry) and a stator 110 (at times referred to as a stationary unit). During an examination of the object(s) 102, the object(s) 102 can be placed on a support article 112, such as a bed or conveyor belt, that is selectively positioned in an examination region 114 (e.g., a hollow bore in the rotor 104), and the rotor 104 can be rotated about the object(s) 102 by a rotator 116 (e.g., motor, drive shaft, chain, etc.).

The rotor 104 may surround a portion of the examination region 114 and may comprise one or more radiation sources 118 (e.g., an ionizing x-ray source, gamma-ray source, etc.) and a detector array 106 that is mounted on a substantially diametrically opposite side of the rotor 104 relative to the radiation source(s) 118. During an examination of the object (s) 102, the radiation source(s) 118 emits fan, cone, wedge, and/or other shaped radiation 120 configurations into the examination region 114 of the object examination apparatus 108. It may be appreciated that such radiation may be emitted substantially continuously and/or may be emitted intermittently (e.g., a short pulse of radiation is emitted followed by a resting period during which the source is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of radiation photons that are detected by the detector array 106. For example, more dense aspects of the object(s) 102, such as a bone or metal plate, may attenuate more of the radiation 120 (e.g., causing fewer photons to be detected by the detector array 106) than less dense aspects, such as skin or clothing.

The detector array 106 is configured to directly convert (e.g., using amorphous selenium and/or other direct conversion materials) and/or indirectly convert (e.g., using photodetectors and/or other indirect conversion materials) detected radiation into signals that can be transmitted from the detector array 106 to a data acquisition component 122 configured to convert the analog signals output by the detector array 106 into digital signals and/or to compile signals that were transmitted within a predetermined time interval, or measurement interval, using various techniques (e.g., integration, photon counting, etc.). It may be appreciated that such a measurement interval may be referred to as a "view" and generally reflects signals generated from radiation 120 that was emitted while the radiation source 118 was at a particular angular range relative to the object 102. Based upon the compiled signals, the data acquisition component 122 can generate projection data indicative of the compiled signals, for example.

Information may be transmitted between components physically attached to the rotor 104 (e.g., such as the detector array 106 and/or data acquisition component 122) and components that are not physically attached to the rotor 104 (e.g., such as an image reconstructor 124) through a data-link. By way of example, the projection space data (at times referred to as image data because it is used to reconstruct images of the object) generated by the data acquisition component 122 may be transmitted via the data-link to an image reconstructor 124 positioned on the stationary side of the imaging modality. As may be described in more detail below, such a data-link typically comprises a transmitting antenna mounted to the rotor 104 and a receiving antenna mounted to the stator 110, where an airgap generally separates the transmitting and receiving antennas from one another.

The image reconstructor 124 is configured to receive the projection space data that is output by the data acquisition component 122 and to generate image space data from the projection data using a suitable analytical, iterative, and/or other reconstruction technique (e.g., backprojection reconstruction, tomosynthesis reconstruction, iterative reconstruction, etc.). In this way, the data is converted from projection space to image space, a domain that may be more understandable by a user 130 viewing the image(s), for example.

The example environment 100 also includes a terminal 126, or workstation (e.g., a computer), configured to receive the image(s), which can be displayed on a monitor 128 to the user 130 (e.g., security personnel, medical personnel, etc.). In this way, a user 130 can inspect the image(s) to identify areas of interest within the object(s) 102. The terminal 126 can also be configured to receive user input which can direct operations of the object examination apparatus 108 (e.g., a speed to rotate, a speed of a conveyor belt, etc.).

In the example environment 100, a controller 132 is operably coupled to the terminal 126. In one example, the controller 132 is configured to receive input from the terminal 126, such as user input for example, and to generate instructions for the object examination apparatus 108 indicative of operations to be performed. For example, the user 130 may desire to reexamine the object(s) 102 at a different energy level, and the controller 132 may issue a command instructing the support article 112 to reverse direction (e.g., bringing the object(s) 102 back into an examination region 114 of the object examination apparatus 108) and instructing a power supply located within the rotor to increase a voltage applied to the radiation source 118 (e.g., causing the radiation output therefrom to have a higher energy).

The data-link is typically comprised of at least four components, a transmitter configured to receive the image data output by the data acquisition component 122 and to prepare/ condition an electrical signal indicative of the data, a transmitting antenna configured to emit radio waves in response to the prepared/conditioned electrical signal, a receiving antenna configured to receive at least some of the emitted radio waves and to generate a radio frequency signal (e.g., a second electrical signal), and a receiver configured to condition the radio frequency signal and/or to convert the radio frequency signal to another transmission medium (e.g., such as an optical signal) for output to the image reconstructor 124, for example.

Figure 2:
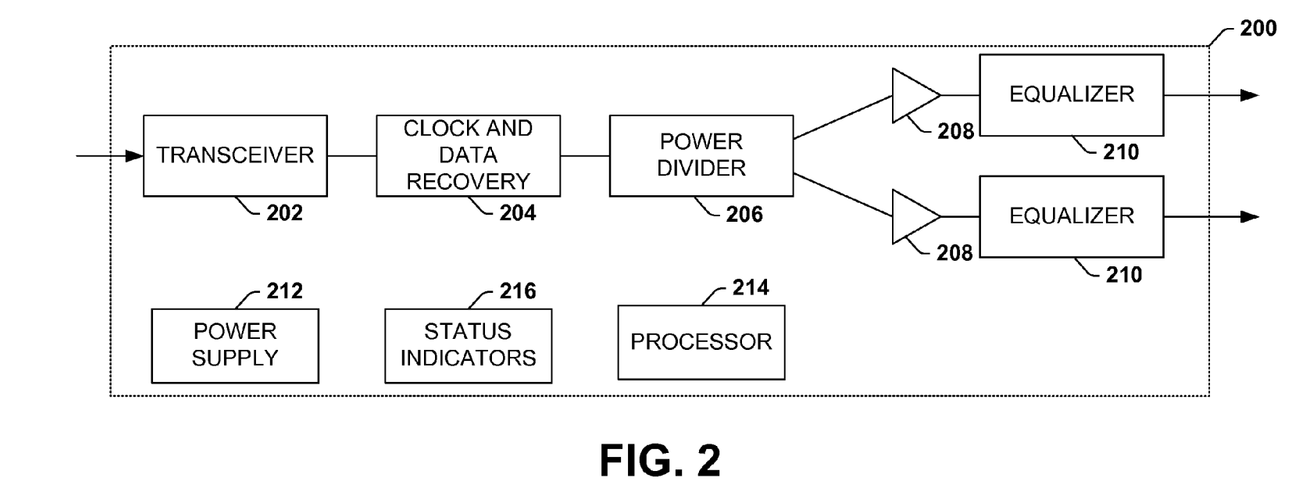
FIG. 2 illustrates a component block diagram of an example transmitter.

FIG. 2 illustrates a component block diagram of an example transmitter 200 configured to receive data via a first transmission medium (e.g., an optical signal) at a transceiver component 202 and to convert the received data into an electrical signal from which radio waves may be generated. It may be appreciated that the components described herein and/or the arrangement of such components is merely intended to provide one example arrangement of a transmitter 200. For example, in another embodiment, the signal received by the transmitter 200 may be an electrical signal and thus the transmitter may not comprise a transceiver configured to convert the signal from an optical signal to an electrical signal. Thus, other arrangements, which may include additional, fewer and/or different components, are also contemplated herein.

The example transmitter 200 comprises, among other things, a transceiver component 202, a clock and data recovery component 204, a power divider component 206, a plurality of amplifiers 208, and a plurality of equalizers 210. Electrical signals output by the equalizers 210 may be respectively output to a transmitting antenna (e.g., which is further described in FIGS. 4-9).

The transceiver component 202 is configured to receive the data via a first transmission medium, such as an optical transmission medium, and to convert the optical signal, for example, into an electrical signal. By way of example and not limitation, in one embodiment, the transceiver component 202 may comprise a fiber channel transceiver configured to receive an optical signal and to convert the optical signal to an electrical signal. However, other converters are also contemplated for converting a signal output by a detector array (e.g., 106 in FIG. 1) and/or by a data acquisition component (e.g., 122 in FIG. 1) into an electrical signal that may be utilized to generate radio waves, for example.

In one embodiment, the signal output by the transceiver component 202 is output without an accompanying clock signal. Therefore, the transmitter 200 may comprise a clock and data recovery component 204 configured to perform a clock and data recovery process on the electrical signal output by the transceiver component 202 to generate an electrical signal that comprises the recovered clock. For example, the clock and data recovery component 204 may be configured to generate a clock (e.g., or recover a clock) from an appropriate frequency reference and to phase-align to the transitions in the signal with a phase-locked loop.

Figure 4:
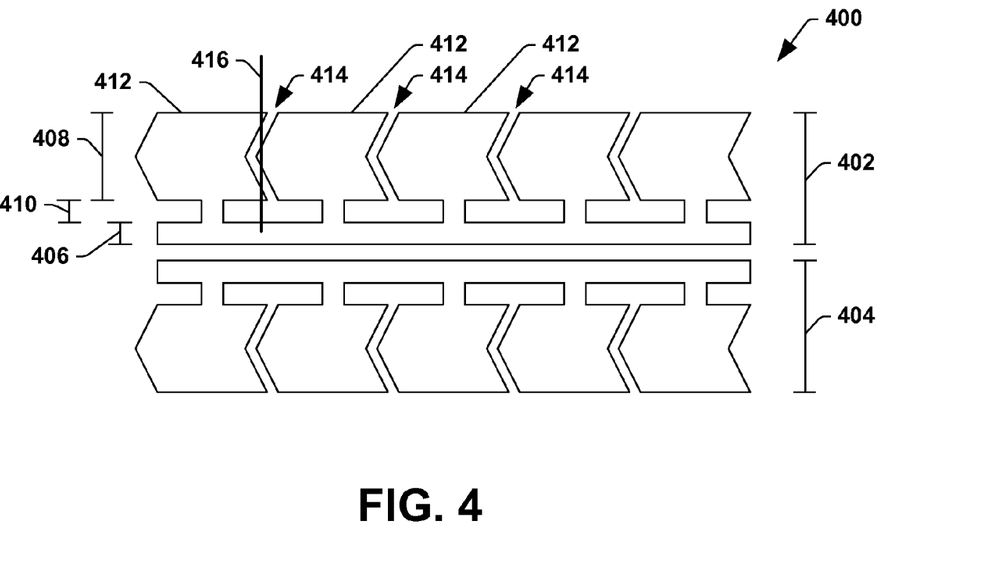
FIG. 4 illustrates an example arrangement of transmitting elements of a transmitting antenna.
Figure 5:
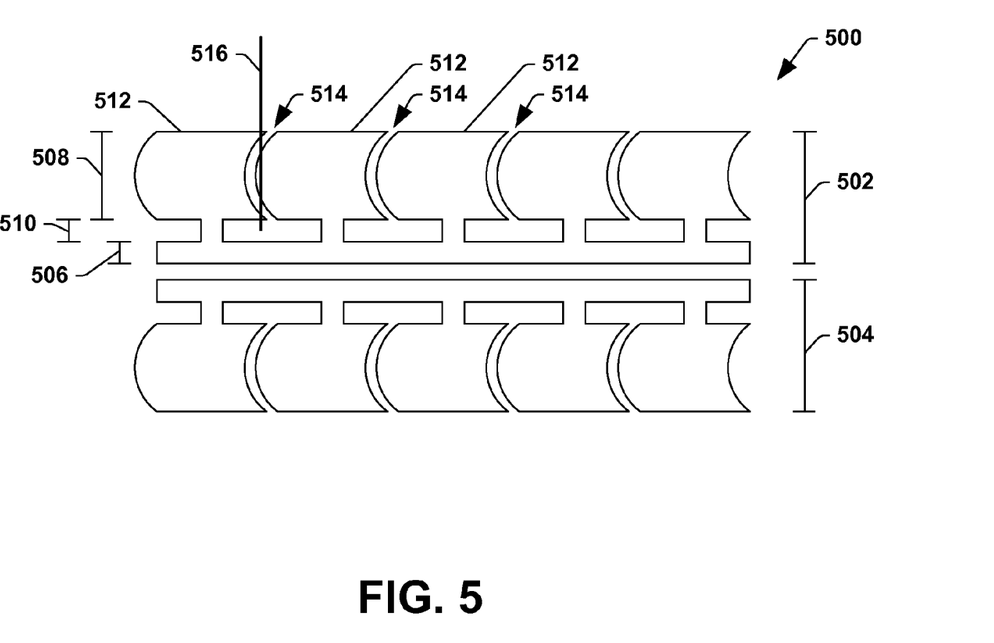
FIG. 5 illustrates an example arrangement of transmitting elements of a transmitting antenna.
Figure 6:
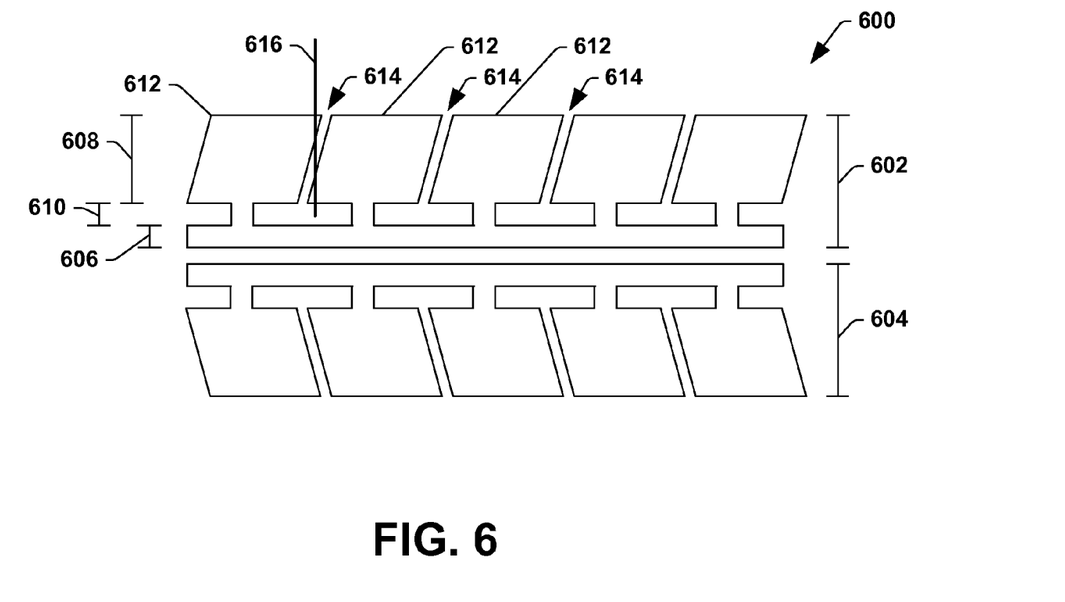
FIG. 6 illustrates an example arrangement of transmitting elements of a transmitting antenna.

As may be described in more detail with respect to FIGS. 4-6, in one embodiment, a transmitting antenna may be comprised of at least two transmitting elements respectively configured to receive an electrical signal from the transmitter 200. As such, in the illustrated embodiment, the transmitter 200 comprises a power divider component 206 configured to divide the electrical signal with the recovered clock into two signals. Typically, the power divider component 206 is configured to divide the signal with the recovered clock into signals having substantially equal amplitudes and phases, although the signals may deviate in amplitude and/or phrase, for example. It may be appreciated that where the transmitting antenna comprises more than two transmitting elements, the power divider component 206 may divide the signal with the recovered clock into more than two signals. Where the transmitting antenna comprises fewer than two transmitting elements, the transmitter 200 may not comprise a power divider component 206, for example.

In the example transmitter 200, respective signals output from the power divider component 206 are transmitted to an amplifier 208 configured to increase the power of the signal. The amplifiers 208 may also serve other functions. For example, in one embodiment, one or more of the amplifiers 208 are drive amplifiers configured to both amplify the power of the signal and to drive the transmitting antenna (e.g., such that respective equalizers 210 operably attached to the amplifiers 208 and/or respective transmitting elements operate at a broad range of input voltages and/or currents, for example).

In the example transmitter 200, the amplified signals output by respective amplifiers 208 are transmitted to an equalizer 210 configured to receive the amplified signals. The equalizers 210 are also configured to, among other things, adjust a balance between frequency components within the electrical signal. That is, the equalizers are configured to strengthen and/or weaken the energy of specific frequency bands to prepare the electrical signals for the transmitting antenna. In this way, the equalizers 210 (and the amplifiers 208) may create electrical signals with a high transmit power to output to the transmitting antennas, for example.

It may be appreciated that the transmitter 200 may further comprise other components that assist the electronic components conditioning the signals and/or that provide information about the conditioning. For example, the transmitter 200 may comprise a power supply 212 configured to provide low voltage power to the transceiver component 202, clock and data recovery component 204, power divider component 206, amplifiers 208, and/or equalizers 210, for example. Moreover, a processor 214 (e.g., such as a microprocessor) may be configured to control and/or configure the clock and data recovery component 204, for example. Further, the processor 214 may be configured to provide operational status indications which may be displayed via a status indicator component 216 (e.g., comprising lights indicative of a current operational status of the transmitter 200).

The one or more signals output by the transmitter 200 may be transmitted to a transmitting antenna configured to convert the electrical signals into radio waves. As will be further detailed with respect to FIGS. 4-6, the transmitting antenna may be comprised of a plurality of transmitting elements, respectively configured to receive an electrical signal and radiate radio waves in response to the received signals. For example, in one embodiment, the transmitting antenna is comprised of at least two transmitting elements, a first transmitting element configured to radiate first radio waves in response to a first of the two signals being applied to the transmitting antenna and a second transmitting element configured to radiate second radio waves in response to a second of the two signals being applied to the transmitting antenna. Thus, in such an embodiment, respective transmitting elements may be configured to convert electrical signals (or currents) comprising an oscillating frequency into radio waves, for example.

Figure 8:
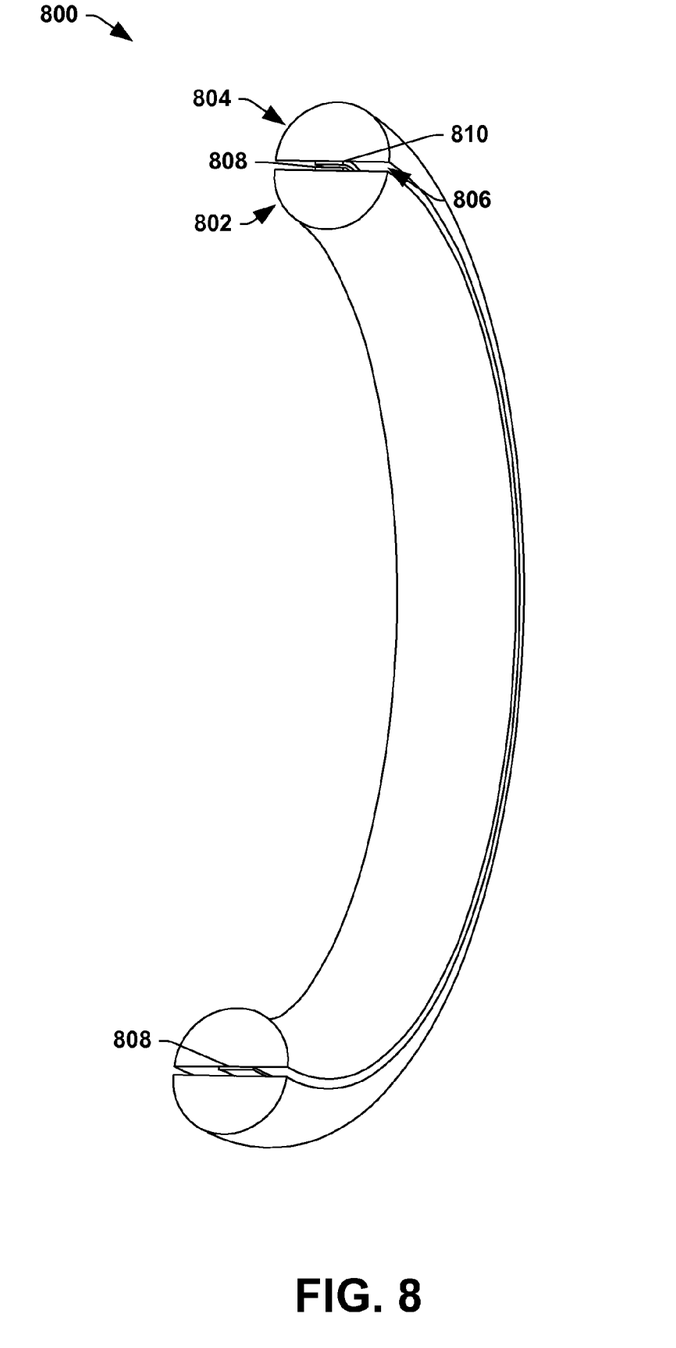
FIG. 8 illustrates an example rotor and stator, with a transmitting antenna being mounted to a radial surface of the rotor.
Figure 9:
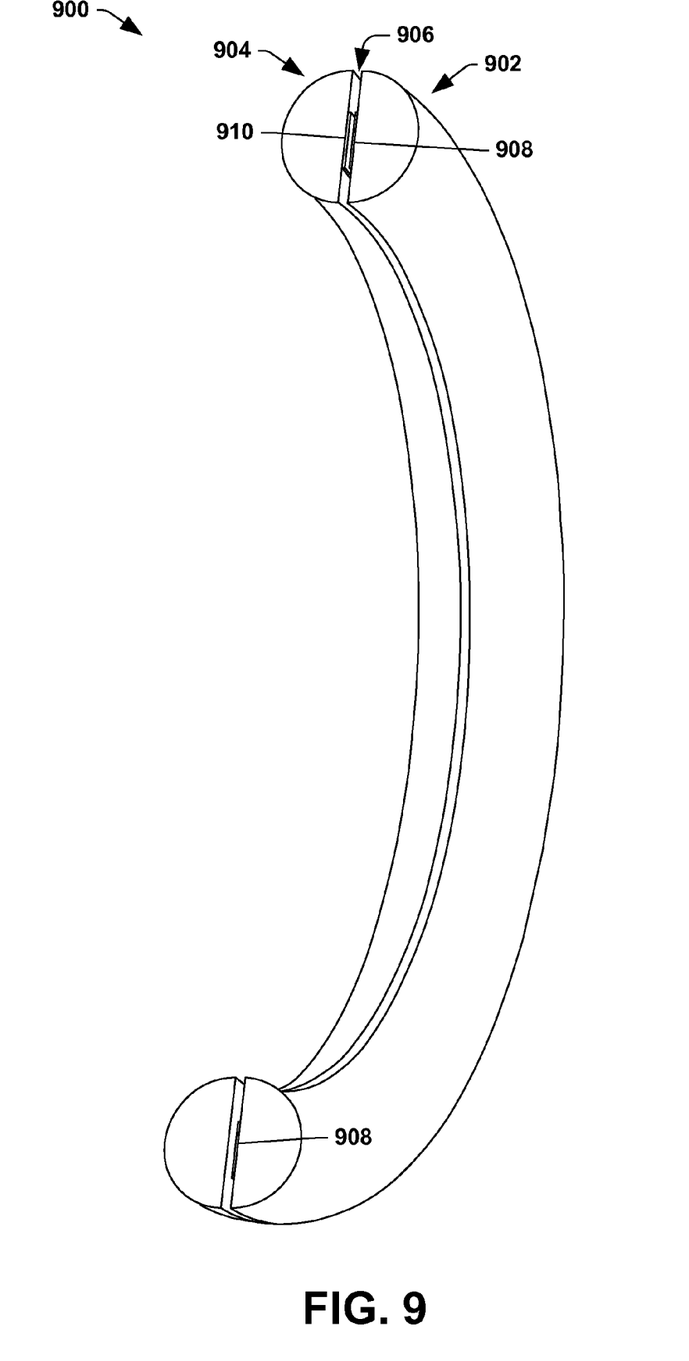
FIG. 9 illustrates an example rotor and stator, with a transmitting antenna being mounted to an axial surface of the rotor.

At least a portion of the radio waves output by the transmitting antenna, or more particularly by respective transmitting elements of the transmitting antenna, may be received by a receiving antenna of the data-link (e.g., which may be separated from the transmitting antenna by an airgap, as will be further described with respect to FIGS. 8 and 9). Like the transmitting antenna, the receiving antenna may be comprised of a plurality of receiving elements. For example, in one embodiment, the receiving elements of the receiving antenna are matched to transmitting elements of the transmitting antenna. Thus, where the transmitting antenna comprises two transmitting elements, the receiving antenna may likewise comprise two receiving elements. Respective receiving elements of the receiving antenna may be configured to generate radio frequency signals (e.g., electrical signals) in response to the detection of radio waves. For example, a first receiving element of the receiving antenna may be configured to generate a first radio frequency signal based upon detected radio waves that were emitted by the first transmitting element of the transmitting antenna and a second receiving element of the receiving antenna may be configured to generate a second radio frequency signal based upon detected radio waves that were emitted by a second transmitting element of the transmitting antenna.

Figure 3:
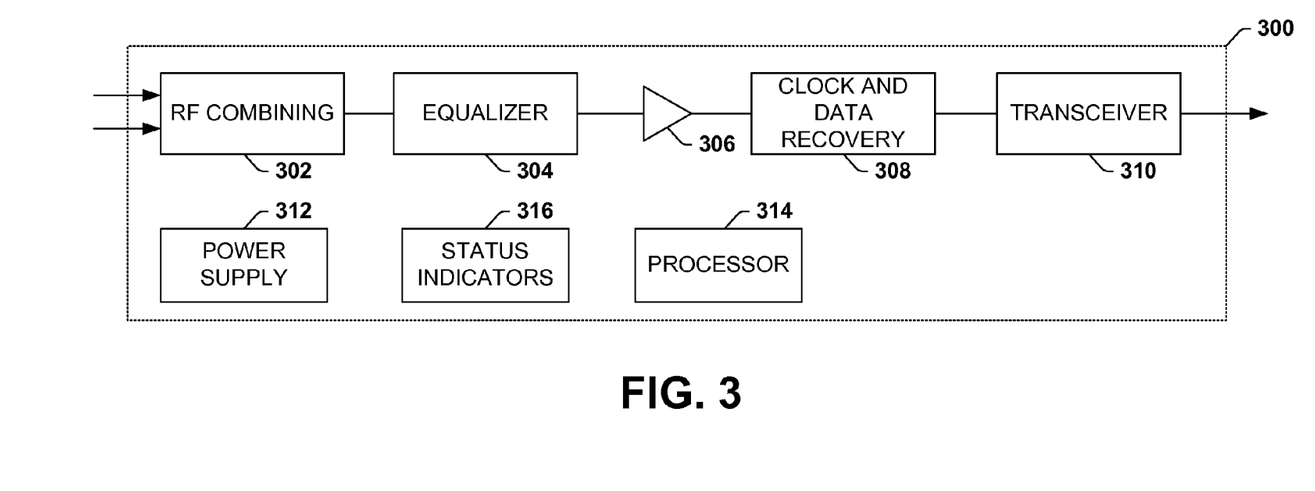
FIG. 3 illustrates a component block diagram of an example receiver.

FIG. 3 illustrates a component block diagram of an example receiver 300 of a data-link configured to receive radio frequency signals output by a receiving antenna, to condition the radio frequency signals, and/or to convert the radio frequency signal to another transmission medium, such as an optical signal, which may be output from the receiver 300 and transmitted to an image reconstructor (e.g., 124 in FIG. 1), for example. It may be appreciated that the components described herein and/or the arrangement of such components is merely intended to provide one example arrangement of a receiver 300. Other arrangements, which may include additional and/or different components, are also contemplated herein.

The example receiver 300 comprises, among other things, a radio frequency combining component 302, an equalizer 304, an amplifier 306, a clock and data recovery component 308, and a transceiver component 310. The radio frequency combining component 302 is configured to combine radio frequency signals generated by two or more receiving elements of the receiving antenna into a combined radio frequency signal (e.g., while maintaining a characteristic impedance of the two or more signals). It may be appreciated that if the receiving antenna merely comprises one receiving element, the receiver 300 may not comprise such a radio frequency combining component 302.

The receiver 300 further comprises an equalizer 304 configured to receive the combined radio frequency signal. The equalizer 304 is also configured to, among other things, adjust a balance between frequency components within the combined radio frequency signal. In this way, the energy of specific frequency bands may be strengthened and/or weakened to prepare the combined radio frequency signal for conversion to an optical signal and/or other transmission medium, for example.

The example receiver 300 also comprises an amplifier 306 configured to increase the power of the combined radio frequency signal. The amplifier 306 may also serve other functions. For example, in one embodiment, the amplifier 306 is a limiting amplifier configured to reduce (e.g., minimize) output power variations while accepting a wide range of input power levels and/or to provide a substantially constant power output over a wide, input dynamic range, for example.

The example receiver 300 further comprises a clock and data recovery component 308 configured to perform a clock and data recovery process on the combined radio frequency signal output by the amplifier 306 to generate a combined radio frequency signal with the recovered clock. For example, the clock and data recovery component 308 may be configured to generate a clock (e.g., or recover a clock) from an appropriate frequency reference and to phase-align to transitions in the signal with a phase-locked loop.

The transceiver component 310 of the receiver 300 is configured to receive the combined radio frequency signal with the recovered clock and to convert the received signal to a different transmission medium, such as to an optical signal. By way of example, in one embodiment, the transceiver component 310 may comprise a fiber channel transceiver configured to convert the combined radio frequency signal with the recovered clock to an optical signal. However, other converters are also contemplated for changing a transmission medium through which the data may be carried, for example.

Moreover, in another embodiment, an image reconstructor (e.g., 124 in FIG. 1) may be configured to receive data via a radio frequency signal and thus that data may not be transitioned to an optical signal, for example.

Like the transmitter 200, the receiver 300 may also comprise other components that assist the electronic components conditioning the signal and/or that provide information about the conditioning. For example, the receiver 300 may comprise a power supply 312 configured to provide low voltage power to the radio frequency combining component 302, the equalizer component 304, the amplifier component 306, the clock and data recovery component 308, and/or the transceiver component 310, for example. Moreover, a processor 314 (e.g., such as a microprocessor) may be configured to control and/or configure the clock and data recovery component 308, for example. Further, the processor 314 may be configured to provide operational status indications, which may be displayed via a status indicator component 316 (e.g., comprising lights indicative of a current operational status of the receiver 300).

FIG. 4 illustrates an example transmitting antenna 400 configured to transmit radio waves between a moveable unit and a stationary unit and/or between two movable units. Such a transmitting antenna 400 may find particularly applicability with radiation imaging modalities, and in particular CT imaging modalities, where image data is transferred from a rotor (e.g., 104 in FIG. 1) to a stator (e.g., 110 in FIG. 1). It may be appreciated that although such an antenna 400 is typically one-directional, information may be transmitted bi-directionally by positioning another transmitting antenna on the stator 110, for example.

The example transmitting antenna 400 comprises two transmitting elements 402 and 404. As illustrated, the transmitting elements 402 and 404 may be mirror images and may be reciprocally and alternatively changed with a substantially same voltage of opposite phase to generate radio waves, for example. However, in other embodiments, the transmitting antenna 400 may comprise merely one transmitting element 402 or may comprise more than two transmitting elements. For example, in another embodiment, the transmitting antenna 400 may comprise multiple pairs of transmitting elements to further increase the throughput of the transmitting antenna 400.

Respective transmitting elements 402 and 404, which may be referred to as wide frequency bandwidth transmitting elements because respective elements are configured to operate at a large spectrum of frequencies (e.g., 100 MHz to several GHz), are comprised of at least two conducting portions 406 and 408. A first conducting portion 406, which may perform as a first capacitive coupling, is configured to conduct signals having a first frequency range (e.g., a high frequency range) and a second conducting portion 408, which may perform as a second capacitive coupling, is configured to conduct signals having a second frequency range (e.g., a lower frequency range). It may be appreciated that while the first and second conducting portions 406, 408 are configured to conduct signals with different frequencies, there may be some overlap in the frequencies of signals that respective conducting portions 406, 408 are configured to conduct. For example, the second conducting portion 408 may be configured to conduct at least some signals that the first conducting portion 406 is configured to conduct and/or vice-versa. Thus, there may be some overlap in the operational frequencies of respective conducting portions 406, 408.

The first conducting portion 406 of respective transmitting elements 402, 404 is configured to be operably coupled to the second conducting portion 408 of respective transmitting elements 402, 404. For example, in the illustrated embodiment, the first conducting portion 406 is operably (e.g., both physically and electronically) coupled to the second conducting portion 408 via a stem 410. Such a stem 410 may perform as a transition between the first conducting portion 406 and the second conducting portion 408.

The second conducting portion 408 of respective transmitting elements 402, 404 is comprised of a plurality of electrically conductive members 412 respectively spaced apart from adjacent members via a (e.g., substantially uniform) gap 414. It may be appreciated that respective members 412 are configured to overlap neighboring members to reduce or mitigate a loss in capacitance (e.g., to increase performance at a lower frequencies where a higher capacitance is useful). That is, respective members 412 are arranged to cause a gradual physical transition between two adjacent members 412, such that, within a region comprising the gap 414, a member 412 at least partially overlaps at least some of an adjacent member 412. In this way, a line 416 drawn through the region comprising the gap 414 contacts at least two members 412 (e.g., one member and a neighboring member). Stated differently, the members 412 are arranged such that, while a gap 414 is maintained, signals crossing the gap 414 transition from a first member 412 to a second member 412 without having to pass through an electrically conductive dead space where there is no conductive material. In this way, the plurality of members 412 are arranged to form a substantially electrically continuous structure while providing for gaps 414 between respective members 412 of the second conducting portion 408.

Given the substantially electrically continuous structure of the second conducting portion 408, it may be appreciated that the loss of capacitance as the signal transitions from a first member 412 to a second member 412 may be reduced (e.g., to zero). That is, stated differently, overlapping, or offsetting, of the members 412 may cause the signal to not enter a period of transition as it moves from a first member 412 to a second member 412, for example.

FIG. 5 illustrates another example of a transmitting antenna 500 of a data-link described herein. Like the transmitting antenna 400 illustrated in FIG. 4, the example transmitting antenna 500 comprises two transmitting elements 502, 504, where a second of the two transmitting elements 504 mirrors the first transmitting element 502. Respective transmitting elements 502, 504 are comprised of at least two conducting portions 506, 508 respectively configured to conduct signals having different frequency ranges (e.g., although there may be some overlap). For example, a first conducting portion 506 may be configured to conduct signals having a first frequency range and a second conducting portion 508 may be configured to conduct signals having a second frequency range. The first and second conducting portions 506, 508 may be operably coupled together via an electrically conductive stem 510 configured to perform as a transition between first and second conducting portions 506, 508, for example.

While continuing with reference to FIG. 5, the second conducting portion 508 may be comprised of overlapping members 512 respectively separated from one another via a (e.g., substantially uniform) gap 514. It may be appreciated that overlap, overlapping and/or the like is intended to describe how an edge of a member 512 is configured and/or arranged relative to an edge of an adjacent member 512 such that a line 516 drawn through at least a portion of the gap 514 intersects at least two adjacent members 512. Thus, the members 512 may be said to overlap even though there is no physical contact between adjacent members. In this way, through the overlap of adjacent members, a substantially electrically continuous structure may be formed from the members 512 even though the members 512 do not form a physically continuous structure (e.g., due to the gaps 514 between respective members).

FIG. 6 illustrates yet another embodiment of an example transmitting antenna 600 of a data-link provided for herein. The illustrated transmitting antenna 600 comprises two transmitting elements 602, 604, where a second of the two transmitting elements 604 mirrors the first transmitting element 602. Respective transmitting elements 602, 604 are comprised of at least two conducting portions 606, 608 respectively configured to conduct signals having different frequency ranges. For example, a first conducting portion 606 may be configured to conduct signals having a first frequency range and a second conducting portion 608 may be configured to conduct signals having a second frequency range. The first and second conducting portions 606, 608 may be operably coupled together via an electrically conductive stem 610 configured to perform as a transition between the first and second conducting portions 606, 608, for example. While continuing with reference to FIG. 6, the second conducting portion 608 may be comprised of overlapping members 612 respectively separated from one another via a gap 614. In this way, a line 616 drawn through at least a portion of the gap 614 intersects two adjacent members 612, for example.

It may be appreciated that FIGS. 4-6 are merely intended to describe example shapes for members that cause a member to at least partially overlap an adjacent member. That is, the instant application, including the scope of the claims, it not intended to be limited to the shapes/patterns illustrated in FIGS. 4-6, and others shapes may exist that create overlapping members as described herein. Moreover, while FIGS. 4-6 illustrate the members as being uniformly shaped, it may be appreciated that the shape and/or size of some members may differ from other members (e.g., within a same transmitting element). Thus, some members of the second conducting portion may be trapezoidal (e.g., as illustrated in FIG. 6) while others are 6-sided (e.g., as illustrated in FIG. 4), for example.

In one embodiment, the conducting portions 606, 608 of respective transmitting elements 602, 604 are mounted to a base plate configured to mechanically support and/or electrically connect components of a transmitting antenna to a transmitter. By way of example, the transmitting elements 602, 604 may be mounted to a printed circuit board.

Figure 7:
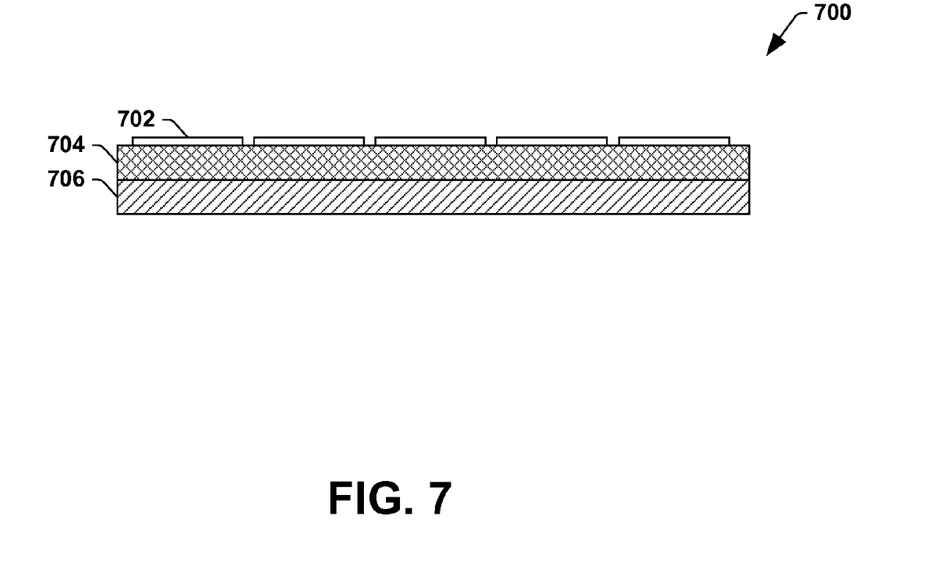
FIG. 7 illustrates an example transmitting antenna comprising of at least one transmitting element and a base plate.

FIG. 7 illustrates an example layout of a base plate 700 (e.g., printed circuit board) from a side-view (e.g., presuming FIGS. 4-6 illustrate a top down view of a transmitting antenna). As illustrated, the base plate or printed circuit board is comprised of at least three layers. The top layer 702 comprises transmitting elements of a transmitting antenna (e.g., 602 and 604 in FIG. 6). The middle layer 704 comprises a dielectric material and the bottom layer 706 comprises a conductive reference ground for mitigating electromagnetic radiation caused by an electrical field created when current passes through the transmitting elements, for example.

The transmitting antenna, including the base plate 700 illustrated in FIG. 7, are configured to be mounted to at least one of a movable unit and a stationary unit. For example, in a radiation imaging modality, where the transmitting antenna is configured to transmit image data from a data acquisition component (e.g., 122 in FIG. 1), the transmitting antenna may be configured to be mounted to the rotor (e.g., 104 in FIG. 1) and a receiving antenna may be configured to be mounted to the stator (e.g., 110 in FIG. 1).

FIG. 8 illustrates a cross-sectional view 800 (e.g., taken along line 8-8 in FIG. 1) of a transmitting antenna 808 that is mounted to a radial surface of a rotor 802 (e.g., 104 in FIG. 1). More particular, the transmitting antenna 808 is mounted to an exterior radial surface of the rotor 802. In another embodiment, the transmitting antenna 808 may be mounted to an interior radial surface of the rotor 802 (e.g., where the interior radial surface defines an outer circumference of a bore into which the object is inserted to be examination).

The rotor 802 is typically separated from a stator 804 (e.g., 110 in FIG. 1) by an airgap 806 that is defined by a space between the rotor 802 and the stator 804 and is configured to enable rotation of the rotor 802 relative to the stator 804. As described above, typically the transmitting antenna 808 is mounted on the rotor 802 within and/or adjacent the airgap 806 and a receiving antenna 810 is mounted on the stator 804 within and/or adjacent the airgap 806. Thus, the transmitting antenna 808 is configured to emit radio waves through the airgap 806 in the direction of the receiving antenna 810, which is positioned on a diametrically opposite side of the airgap 806 relative to the transmitting antenna 808. The distance between the transmitting antenna 808 and the receiving antenna 810 may be small given that the airgap 806 is typically less than 20 mm, although it may be more than 20 mm (e.g., such as up to a few inches).

In applications where the transmittal distance is small, such as in radiation imaging modalities, typically at least one of the transmitting antenna 808 and the receiving antenna 810 extends along substantially an entire surface of the rotor 802 and/or the stator 804 (e.g., forming a nearly complete ring). For example, in the illustrated embodiment, the transmitting antenna 808 is configured to extend along an outer circumference of the rotor 802 while the receiving antenna 810 is mounted to merely a small portion of an inner circumference of the stator 804 (e.g., where the receiving antenna 810 is shown as being comprised in a top portion of the stator 804 but not a bottom portion (absence of reference character 810 in the bottom of FIG. 8)). In this way, as the rotor 802, including the transmitting antenna 808, rotates, a portion of the transmitting antenna 808 remains in close spatial proximity to the receiving antenna 810 (e.g., which may not form a complete or nearly complete ring along an inner surface of the stator 804).

It may be appreciated that where the transmitting antenna 808 forms a nearly complete ring around a bore of the radiation imaging modality through which an object is examined, the transmitting antenna 808, including a base plate, transmitting elements, and/or conducting portions of transmitting elements, may be said to be annular. Moreover, components of the transmitting antenna 808, such as the conducting portions of respective transmitting elements, that extend along the length of the transmitting antenna (e.g., where the length is measured as the circumference of the nearly complete ring) may be considered concentric because they share a common axis. Moreover, this common axis may be parallel with an axis of rotation for the rotor 802, for example.

FIG. 9 illustrates a cross-sectional view 900 of another embodiment for mounting a transmitting antenna 908 to a movable and/or stationary unit. More particularly, FIG. 9 illustrates the transmitting antenna 908 as being mounted to an axial surface of a rotor 902.

While continuing with reference to FIG. 9, typically at least one of the transmitting antenna 908 and a receiving antenna 910 extends along substantially an entire surface of the rotor 902 and/or a stator 904 (e.g., forming a nearly complete ring). For example, in the illustrated embodiment, the transmitting antenna 908 follows the circumference of the rotor 902, while the receiving antenna 910 is mounted to merely a small portion of an axial surface of the stator 904 (e.g., where the receiving antenna 910 is shown as being comprised in a top portion of the stator 904 but not a bottom portion (absence of reference character 910 in the bottom of FIG. 9)). In this way, as the rotor 902, including the transmitting antenna 908, rotates, a portion of the transmitting antenna 908 remains in close spatial proximity to the receiving antenna 910 (e.g., which may not form a complete or nearly complete ring along an axial surface of the stator 904) and transmits radio waves through an airgap 906.

It may be appreciated that various advantages may arise based upon the placement of the antennas. For example, a transmitting antenna mounted to an interior radial surface of a rotor may be shorter in length than a transmitting antenna mounted on an exterior radial surface and/or an axial surface (e.g., meaning that there may be fewer losses in the transmitting antenna). However, a base plate, such as a printed circuit board, mounted to the interior radial surface may be required to be more flexible than a printed circuit board mounted elsewhere (e.g., due to the degree to which the printed circuit board is bent to mount the transmitting antenna to the interior radial surface). Moreover, depending upon, among other things, the placement of the transmitting antenna, the transmitting antenna may be comprised of a plurality of segments that are operably coupled together. For example, a transmitting antenna mounted to an axial surface of the rotor may comprise a segmented printed circuit board (e.g., respectively comprising a portion of the first conducting portion of a transmitting element and a portion of the second conducting portion) that is operably coupled together. Thus, the transmitting antenna may be constructed of segments of printed circuit boards measuring less than two feet apiece, as opposed to a printed circuit board measuring four feet of more (e.g., which may be much more costly to manufacture and/or purchase), for example.

The words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A wide frequency bandwidth transmitting element for a radiation imaging modality, comprising:
    a first conducting portion configured to conduct signals having a first frequency range and extending in a first direction; and
    a second conducting portion configured to conduct signals having a second frequency range, the second conducting portion comprising a plurality of members arranged in a column extending in the first direction, and wherein
    wherein the first conducting portion and the second conducting portion are substantially annular;
    the first conducting portion is electrically coupled to the second conducting portion, and
    a first member of the plurality of members overlaps a second member of the plurality of members in a second direction substantially perpendicular to the first direction.

2. The wide frequency bandwidth transmitting element of claim 1, wherein a first sidewall of the first member is concave, the first sidewall of the first member facing the second member.

3. The wide frequency bandwidth transmitting element of claim 2, wherein a first sidewall of the second member is convex, the first sidewall of the second member facing the first member.

4. The wide frequency bandwidth transmitting element of claim 3, further comprising an airgap between the first sidewall of the first member and the first sidewall of the second member.

5. The wide frequency bandwidth transmitting element of claim 1, further comprising a first stem electrically coupling and physically coupling the first conducting portion to the first member.

6. The wide frequency bandwidth transmitting element of claim 5, further comprising a second stem electrically coupling and physically coupling the first conducting portion to the second member.

7. The wide frequency bandwidth transmitting element of claim 1, wherein a first sidewall of the first member is defined by a first surface having a positive slope and a second surface having a negative slope, the first sidewall of the first member facing the second member.

8. The wide frequency bandwidth transmitting element of claim 1, further comprising an airgap between a sidewall of the first member facing the second member and a sidewall of the second member facing the first member.

9. The wide frequency bandwidth transmitting element of claim 1, further comprising a printed circuit board to which the first conducting portion and the second conducting portion are mounted.

10. The wide frequency bandwidth transmitting element of claim 9, the printed circuit board comprising a dielectric layer and a conductive reference ground layer, wherein:
    the dielectric layer comprises a top surface and a bottom surface,
    the first conducting portion and the second conducting portion are mounted to the top surface, and
    the conductive reference ground layer is mounted to the bottom surface.

11. The wide frequency bandwidth transmitting element of claim 9, wherein the printed circuit board is divided into two or more segments, wherein:
    a first segment of the two or more segments comprises a first portion of the first conducting portion and a first portion of the second conducting portion; and
    a second segment of the two or more segments comprises a second portion of the first conducting portion and a second portion of the second conducting portion.

12. A data-link for a CT imaging modality, comprising:
    a transmitter, comprising:
        a transceiver component configured to convert an optical signal indicative of an examination of an object by the CT imaging modality into an electrical signal,
        a clock and data recovery component configured to recover a clock from the electrical signal and to generate an electrical signal with the recovered clock, and
        a power divider component configured to divide the electrical signal with the recovered clock into two signals;
    a transmitting antenna comprising at least two transmitting elements, a first transmitting element of the at least two transmitting elements configured to radiate first radio waves in response to a first of the two signals and a second transmitting element of the at least two transmitting elements configured to radiate second radio waves in response to a second of the two signals;
    a receiving antenna configured to receive the first and second radio waves, a first radio frequency signal being generated from the first radio waves and a second radio frequency signal being generated from the second radio waves; and
    a receiver, comprising:
        a radio frequency combining component configured to combine the first and second radio frequency signals and generate a combined radio frequency signal,
        a clock and data recovery component configured to recover a clock from the combined radio frequency signal and generate a combined radio frequency signal with the recovered clock, and
        a transceiver component configured to convert the combined radio frequency signal with the recovered clock to an optical signal.

13. The data-link of claim 12, the transmitter further comprising:
    an amplifier configured to amplify at least one of the two signals, and
    an equalizer configured to equalize an amplified signal.

14. The data-link of claim 12, the receiver further comprising:
    an equalizer configured to equalize the combined radio frequency signal.

15. The data-link of claim 12, at least one of the at least two transmitting elements comprising a first conducting portion and a second conducting portion, the first conducting portion configured to radiate radio waves within a first frequency range and the second conducting portion configured to radiate radio waves within a second frequency range, the first frequency range different than the second frequency range.

16. The data-link of claim 15, the second frequency range comprising at least some frequencies that are less than at least some frequencies comprised in the first frequency range, and the second conducting portion comprising a plurality of members, the plurality of members arranged such that a first member of the plurality of members overlaps at least some of a second member of the plurality of members.

17. The data-link of claim 15, the second frequency range comprising at least some frequencies that are less than at least some frequencies comprised in the first frequency range, and the second conducting portion comprising a plurality of members, the plurality of members arranged to form a substantially electrically continuous structure.

18. A CT imaging modality, comprising:
   a rotating gantry configured to rotate about an object under examination, the rotating gantry comprising:
      a radiation source configured to emit radiation towards the object under examination;
      a detector array configured to detect at least a portion of the emitted radiation and to generate analog signals indicative of the detected radiation;
      a data acquisition system configured to convert the analog signals into data; and
      a transmitting element configured to radiate radio waves in response to electrical signals, corresponding to at least some of the data, applied to the transmitting element, the transmitting element comprising at least first and second conducting portions,
      the first conducting portion configured to conduct radio frequency signals having a first frequency range and the second conducting portion configured to conduct radio frequency signals having a second frequency range, the second frequency range comprising at least some frequencies that are less than at least some frequencies comprised in the first frequency range,
      the first conducting portion electrically coupled to the second conducting portion, and
      the second conducting portion comprised of a plurality of members, the plurality of members arranged such that at least some of a first member of the plurality of members overlaps at least some of a second member of the plurality of members.

19. The CT imaging modality of claim 18, further comprising a printed circuit board, the at least first and second conducting portions mounted to the printed circuit board, the printed circuit board comprising a dielectric layer and a conductive reference ground layer, the dielectric layer comprising a top surface and a bottom surface, the at least first and second conducting portions mounted to the top surface and the conductive reference ground layer mounted to the bottom surface.

20. The CT imaging modality of claim 18, wherein the radiation source comprises an ionizing radiation source.

* * * * *